United States Patent [19]

Sims

[11] Patent Number: 4,840,479
[45] Date of Patent: Jun. 20, 1989

[54] CROSSED CYLINDER LENSES REFRACTOR WITH THREE-LENS VARIABLE CROSSED CYLINDER ASSEMBLY AND METHOD OF USE

[76] Inventor: Clinton N. Sims, 3432 W. Riverside Dr., Ft. Myers, Fla. 33901

[21] Appl. No.: 116,322

[22] Filed: Nov. 2, 1987

Related U.S. Application Data

[63] Continuation-in-part of Ser. No. 23,980, Mar. 16, 1987, which is a continuation of Ser. No. 670,398, Nov. 9, 1984, abandoned.

[51] Int. Cl.⁴ .............................................. A61B 3/02
[52] U.S. Cl. .................................... 351/235; 351/234
[58] Field of Search ............... 351/233, 234, 235, 246, 351/216, 217, 218, 227, 228, 229, 230, 231

[56] References Cited

U.S. PATENT DOCUMENTS

| | | |
|---|---|---|
| 579,132 | 3/1897 | Clark . |
| 2,874,610 | 2/1959 | Wright . |
| 2,923,200 | 2/1960 | Wright . |
| 2,938,426 | 5/1960 | Armbruster et al. . |
| 2,968,213 | 1/1961 | Wright et al. . |
| 2,995,065 | 8/1961 | Wright et al. . |
| 3,015,988 | 1/1962 | Hemstreet . |
| 3,136,839 | 6/1964 | Safir . |
| 3,415,594 | 12/1968 | Aulhorn . |
| 3,428,398 | 2/1969 | Gottschalk . |
| 3,498,699 | 3/1970 | Wilkinson . |
| 3,524,702 | 8/1970 | Bellows et al. . |
| 3,572,908 | 3/1971 | Grolman . |
| 3,602,580 | 8/1971 | Samuels . |
| 3,664,631 | 5/1972 | Guyton . |
| 3,785,723 | 1/1974 | Guyton . |
| 3,791,719 | 2/1974 | Kratzer et al. . |
| 3,819,256 | 6/1974 | Bellows et al. . |
| 3,822,932 | 7/1974 | Humphrey . |
| 3,832,066 | 8/1974 | Cornsweet . |
| 3,841,760 | 10/1974 | Guyton . |
| 3,860,330 | 1/1975 | Persson . |
| 3,874,774 | 4/1975 | Humphrey . |
| 3,880,502 | 4/1975 | Humphrey . |
| 3,883,233 | 5/1975 | Guilino . |
| 3,969,020 | 7/1976 | Lynn et al. . |
| 4,021,102 | 5/1977 | Iizuka . |
| 4,105,302 | 8/1978 | Tate, Jr. . |
| 4,179,196 | 12/1979 | Persson et al. . |
| 4,180,323 | 12/1979 | Persson et al. . |
| 4,185,896 | 1/1980 | Buhler . |
| 4,190,332 | 2/1980 | Body et al. . |
| 4,215,919 | 8/1980 | Rybicki . |
| 4,385,813 | 5/1983 | Klein et al. . |
| 4,413,891 | 11/1983 | Rybicki . |
| 4,426,140 | 1/1984 | Stephens . |
| 4,436,390 | 3/1984 | Aoki . |
| 4,496,226 | 1/1985 | Augusto et al. . |
| 4,523,822 | 6/1985 | Thurston . |
| 4,606,624 | 8/1986 | Wood . |

FOREIGN PATENT DOCUMENTS 598683  5/1960  Canada .
820766  9/1959  United Kingdom .

OTHER PUBLICATIONS

Stokes, "On a Mode of Measuring the Astigmatism of a Defective Eye" (1883).
Dennett, "The Stokes' Lens for Measuring Astigmatism" (1885).
Jackson, "A Trial Set of Small Lenses in a Modified Trial Frame" (1887).

(List continued on next page.)

*Primary Examiner*—Rodney B. Bovernick
*Attorney, Agent, or Firm*—Kilpatrick & Cody

[57] ABSTRACT

A new lens system and method of use for otherwise conventional refractors comprising a synchronized, three-lens, variable crossed cylinder lens attachment and selectable fixed crossed cylinders which may be placed in the examining optical path. The synchronized, variable crossed cylinder lens attachment replaces the Jackson crossed cylinder lens and rotates in step with rotation of the cylinder lens axis. Batteries of strong and weak crossed cylinder lenses replace the strong and weak cylinder lenses of conventional refractors. Refractive techniques utilizing the disclosed crossed cylinder lens systems are also described.

21 Claims, 4 Drawing Sheets

OTHER PUBLICATIONS

"Dr. Thomson's 1895 Correspondence Course in Optics with Historical Commentary by Monroe J. Hirsch".

Friedman, "The Jackson Crossed Cylinder, A Critique" (1940).

Crisp, "A New Cross-Cylinder Test for Astigmatic Axis, Without Use of Test Type" (1942).

Egan, "A Resume of Crossed Cylinder Application and Theory".

Littmann, "Fundamental Considerations About Opthalmometry".

Wunsh, "The Crossed Cylinder" (chapter 38 of *Clinical Ophthalmology* (vol. 1), Duane, editor (1978).

Kaufman, "Subjective Refraction: Fogging Use of the Astigmatic Dials" (chapter 39 of Clinical Ophthalmology (vol. 1), Duane, editor (1978).

Duke-Elder and Abrams, "Ophthalmic Optics in Refraction" (1970), pp. 438–439.

Alverez, "Development of Variable—Focus Lenses and a New Refractor" (1978).

Michaels, Visual Optics and Refraction (chapter 12) (1980).

Guyton, "Automated Clinical Refraction" (chapter 67 of *Clinical Ophthalmology* (vol. 1), Duane, editor (1985).

CROSSED CYLINDER LENSES REFRACTOR WITH THREE-LENS VARIABLE CROSSED CYLINDER ASSEMBLY AND METHOD OF USE

CROSS-REFERENCE TO RELATED APPLICATION

This application is a continuation-in-part of application Ser. No. 07/023,980 filed Mar. 16, 1987, entitled "Crossed Cylinder Lenses Refractor and Method of Use," which application is a continuation of application Ser. No. 06/670,398 filed Nov. 9, 1984, both of which applications are incorporated herein in their entirety by this reference.

FIELD OF THE INVENTION

This invention relates to objective optical refractors used to determine the refractive errors in the eyes of humans.

BACKGROUND OF THE INVENTION

A refractor is a known ophthalmic instrument typically having batteries of trial lenses used to determine and remedy the refractive errors of a patient's eye. In modern refractors there are similar left and right batteries which include lens disks or cells containing lenses of spherical and cylindrical power, means for rotating the lens cells to place a lens or a combination of lenses before the eye under examination and a means for setting the axis of the cylinder lens. A modern refractor typically also includes a synchronized Jackson crossed cylinder to be used as a check test for the neutralization of astigmatism (cylinder power and axis), as well as auxiliary lenses.

Techniques for refracting utilizing the Jackson crossed cylinder and the various spheres and cylinders of the refractor are well known. As refraction is presently practiced, the patient's refractive error is expressed in a sphere and a cylinder at a certain axis, which in reality represents the spherical equivalent plus the final crossed cylinder at a certain axis that is required to neutralize the patient's refractive error.

Present refractors are designated as having either positive or negative cylinders. Techniques of refracting have been designed to utilize the negative cylinders (negative theory of refracting). The negative theorem can be converted for the use of positive cylinders (positive theory of refracting) but is awkward. Similar techniques for retinoscopy have been developed mainly for positive cylinders. Both the negative and positive cylinders can be utilized in a manifest refraction when a meridional straddle is maintained. This final manifest refraction is the most accurate, as well as the most time consuming part of the refraction technique. It is the manifest refraction from which the final refraction is determined in cooperative patients, which probably comprise 95% of the average opthalmologist's and optometrist's refraction cases.

A well known problem for refractionists in performing the manifest refraction is maintaining a meridional balance throughout the manifest refraction. In the technique commonly performed with the conventional refractor, the refractionist is required to move one spherical lens and two cylindrical lenses in order to show the patient two images which are different by a minimum cylindrical correction.

However, a significant optical error is introduced by conventional refractors during refraction of patients having an astigmatic error in accordance with this technique. A 0.125D spherical equivalent jump of the images presented to the patient occurs when such refractors are used in the final manifest refraction by presenting successive cylinder lenses. This spherical equivalent jump occurs because cylinder lenses have a spherical component (equal to one-half of the cylindrical component of opposite sign), and conventional trial lenses are graded in 0.25 diopter increments. Thus, successive cylinder lenses change the resulting spherical component by 0.125 diopter, which means the exact meridional balance can be retained only with every other cylinder increment. The problem for the patient is that the two crossed cylinder images presented to him are different by a spherical equivalent of 0.125D, and produce an inequality in image shape, i.e. the circle of least confusion becomes oval. That is, if one crossed cylinder image is a circle, the other image is an oval. The images are therefore dissimilar. (This visual comparison is obvious when a video camera, which is made astigmatic, is refracted. One image is in focus and the other is out of focus.) With the negative cylinder technique of refracting, accommodation is introduced every other time the cylinder power is changed, and with the positive cylinder technique of manifest refracting, a fog is introduced every other time the cylinder power is changed.

The refractionist can make the image comparisons for the patient equal or constant, that is comparing circles to circles or ovals to ovals by introducing a 0.125D sphere auxiliary lens. However, this requires the refractionist to change five lenses (two auxiliary lenses, one spherical lens and two cylindrical lenses) in order to show the patient just two similar images of no spherical equivalent difference and of a circle of least confusion that is decreasing or increasing in size. Thus, a technique utilizing an auxiliary lens in this manner is impractical and confusing in practice.

U.S. Pat. No. 4,385,813, to Klein, et al., teaches a computerized refractor using sphere and cylinder lenses and intended to solve the refractor manipulation problems presented by conventional refractors, but this approach is expensive and does not prevent the 0.125D spherical jump described above, although it could perhaps be adapted to accomplish that with different programming or different lenses.

Another problem that the refractionist has is the inability to maintain the same meridional balance while using the Jackson crossed cylinder in order to check the cylinder power. If a fog is produced, as with the positive cylinder phoropters, the refractionist may be inclined to prescribe too much against-the-rule astigmatism Theoretically, it is also possible to prescribe too much with-the-rule astigmatism when negative cylinders are used with a Jackson crossed cylinder in an eye which has had a cycloplegic.

Refraction in accordance with conventional techniques is particularly difficult where the patient and refractionist do not speak the same language because of the difficulty of communicating, even through a translator, during the complex series of comparisons necessary in the conventional refraction.

Another problem the refractionist has is the inability of many patients, especially older ones, to respond to the use of astigmatic dials. The reason for this difficulty is obvious when one realizes that the theory of the astigmatic dial is based on the conoid of Sturm, which exists only in a thin lens system, whereas the eye is a complicated thick lens system.

An additional problem that the refractionist has is teaching a technician or student to refract, which takes many years of experience. Computerized objective/subjective refractors have reduced this obstacle; however their cost is high, their accuracy debatable, and it is questionable whether such refractors increase refraction efficiency.

The mechanics of moving the lens wheels of the phoropter is most confusing and difficult to teach technicians and ophthalmologists. It is very important to the refractionist to be able to maintain the same system of lens changes when he increases and/or decreases the crossed cylinder powers while maintaining the spherical equivalent.

SUMMARY OF THE INVENTION

The above mentioned problems experienced by the patient and refractionist are avoided or solved by use, as is described in my previous application Ser. Nos. 06/670,398 and 07/023,980, of a synchronized variable crossed cylinder attachment for a refractor and/or a refractor using selectable crossed-cylinder lenses rather than the cylinder lenses conventionally used.

The synchronized variable crossed cylinder attachment or assembly disclosed in my previous applications comprises two crossed cylinder lenses, or two cylinder lenses of equal power but opposite sign, mounted so as to be positionable in front of the viewing tube of the refractor. The lenses are rotatable in opposite directions at equal rates, and the resulting axis of the lens pair is synchronized to rotate in step with rotation of cylinder lenses in the cylinder lens discs of the refractor.

Additional advantages may be achieved by modification of this variable crossed cylinder assembly in accordance with the present invention to use one stationary positive cylinder lens in the assembly with two equal-power, counter-rotating negative cylinder lenses, each having a negative power equal to one-half of the power of the positive lens. Alternatively, a negative stationary lens can be used with positive rotating lenses. Crossed cylinder lenses may also be used rather than cylinder lenses. The improvement of the present invention enhances the accuracy of measurement of astigmatism by spreading the angular separation of the positions of the counter-rotating lenses for a given cylinder power change and by increasing the crossed cylinder power range as compared to my previously described structure.

As were the objectives of my invention disclosed in my previous applications, it is also an object of the present invention to provide a simple solution to the problems of the refractionist and the patient described above, by providing a simple manual refractor that will eliminate unequal visual comparisons.

Another object of the present invention is to provide the refractionist a faster technique of varying the crossed cylinders while maintaining the same spherical equivalent. With the replacement of the conventional cylinders in a refractor with the crossed cylinders, not only is the 0.125D image jump eliminated, but the refractionist is also able to maintain a perfect meridional straddle by changing only one lens (crossed cylinder) instead of three lenses (the auxiliary lens, the sphere lens and the cylinder lens) per change of the refraction crossed cylinder while maintaining the same spherical equivalent.

An advantage of the invention is that practice of the two theorems of refracting (positive and negative cylinders) become the same when a perfect meridional balance is maintained after a spherical equivalent is determined.

A further advantage of the invention is that the technique of fogging is eliminated by scanning for astigmatism in 40° increments with the selectable crossed cylinder lenses or with the synchronized variable crossed cylinder lens assembly. The synchronized crossed cylinder lens system of the present invention allows the refractionist to show the patient several hundred crossed cylinder powers at different angles in a matter of only a few seconds. If astigmatism is detected, it may then be confirmed with the selectable crossed cylinder lenses in refractor at the determined axis. This technique of refracting is similar to that taught in U.S. Pat. No. 4,385,813, to Klein, et al., which is incorporated herein by reference; however, Klein, et. al. requires a computer and step motor-controlled refractor and does not use crossed cylinder lenses as taught in the present invention.

Another advantage of the present invention is that the technique of "crossed cylinder fogging" is faster, as well as mechanically easier, with the use of the selectable crossed cylinder lenses and/or the synchronized variable crossed cylinder lens assembly disclosed.

An additional advantage of the present invention is the elimination of the iatrogenic induction of with-the-rule or against-the-rule astigmatism inherent with the Jackson crossed cylinder refraction technique when a perfect meridional balance is not maintained as in previous techniques.

A further advantage of the synchronized variable crossed cylinder lens assembly of the present invention is the replacement of the error-prone, audio-visual responses that are required with conventional refractors with a silent visual response.

Another advantage of the present invention is that the synchronized variable crossed cylinder lens assembly allows the refractionist to detect and neutralize any astigmatism many times faster than is presently possible.

Other advantages to the refractionist are:

The use of cycloplegics is rarely required, even for the young patient.

Objective refractors are not required to obtain an initial beginning point for the manifest refraction.

Retinoscopy is rarely required to perform an endpoint manifest refraction.

The time required to perform a manifest refraction for pathological or non-pathological patients is very significantly decreased.

The accuracy of refraction is significantly improved, thus reducing the optical remake rate.

Other objects, features and advantages of the present invention will become apparent with reference to the remainder of the specification, claims and drawings.

DETAILED DESCRIPTION OF THE DRAWINGS

Figure 1:
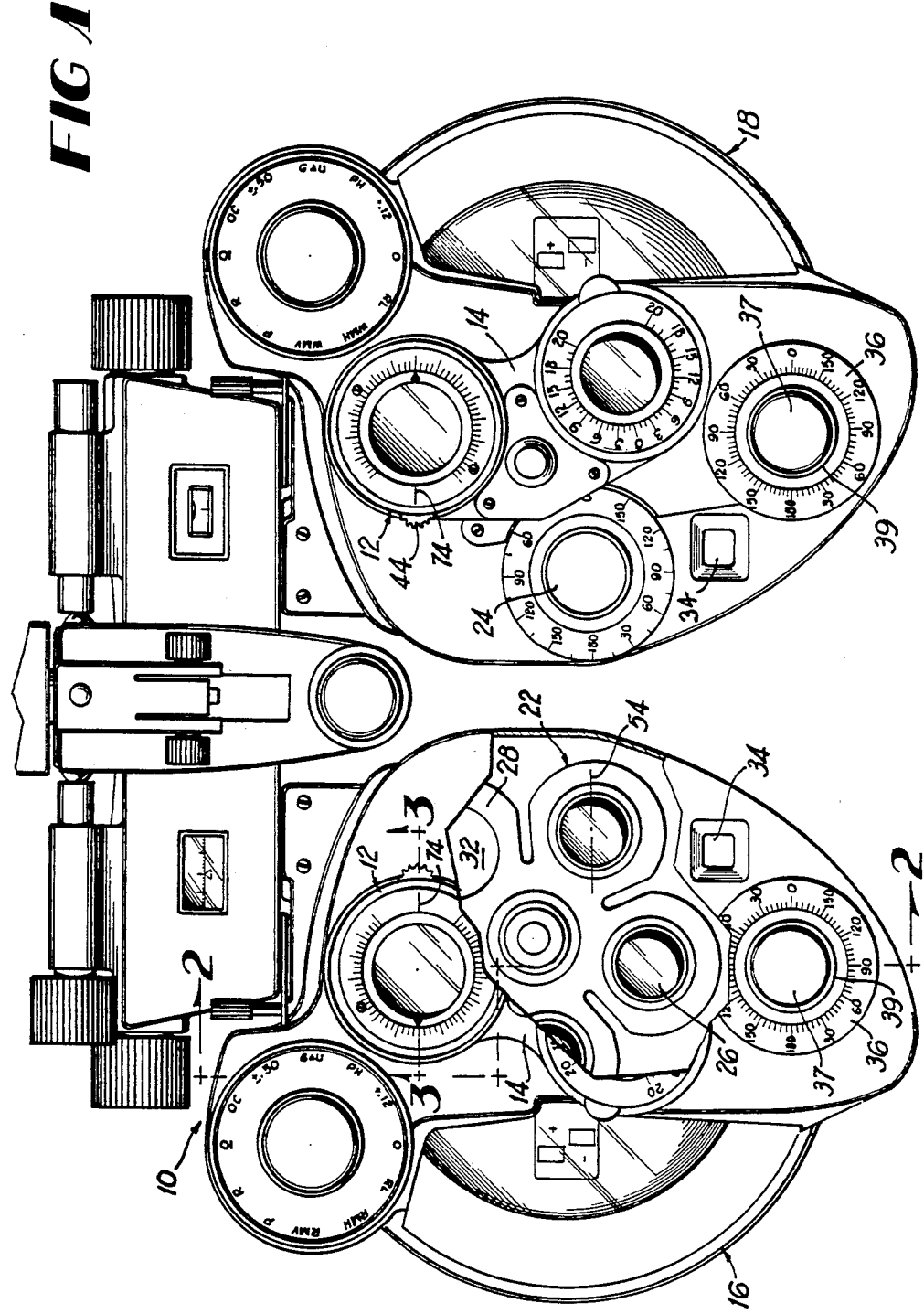
FIG. 1 is a front view of a substantially conventional refractor taken from the practitioner's side of the instrument showing the synchronized variable crossed cylinder lens assembly of the present invention attached to the yoke of the refractor, and showing the left eye battery in elevation and the right eye battery partly in elevation and partially broken away to reveal the forward crossed cylinder lens disk.
Figure 2:
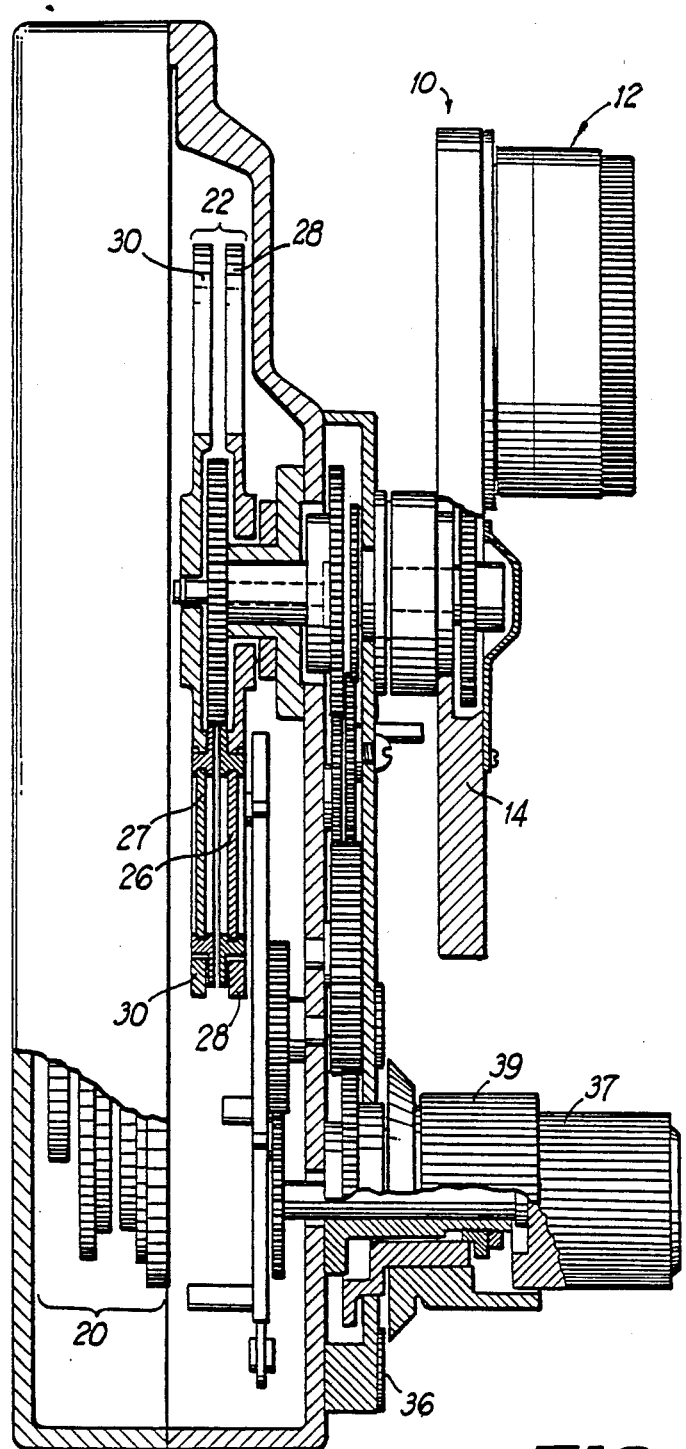
FIG. 2 is a cross-sectional view of the right eye battery taken substantially along the lines 2—2 of FIG. 1, illustrating the selectable crossed cylinder assembly and the synchronized variable crossed cylinder assembly of the present invention.

FIG. 1 is a front view of a substantially conventional refractor 10. The refractor 10 includes a right eye battery 16 and a left eye battery 18, these batteries may be essentially identical. FIG. 1 shows the synchronized variable crossed cylinder lens attachment, or assembly 12 the present invention attached to the yoke or turret 14 the refractor, and the right eye battery 16 is partially broken away to show the selectable crossed cylinder lens system 22 of the present invention, which is also identified on FIG. 2. Only the synchronized variable crossed cylinder lens assembly 12 and the selectable crossed cylinder lens system 22 of the present invention as incorporated in an otherwise conventional refractor 10 will be discussed. FIG. 1 shows the refractor 10 from the refractionist's side, and this side will be referred to as the front side of the instrument.

The major component parts of each battery 16 and 18 (see FIGS. 1 and 2) include a sphere lens assembly 20, a selectable crossed cylinder lens assembly 22 and a synchronized variable crossed cylinder attachment 12. The patient positions his head to the rear of the instrument so that each of his eyes is in alignment with the viewing tubes 24.

SELECTABLE CROSSED CYLINDER LENS ASSEMBLY

The selectable crossed cylinder lens assembly 22 may comprise crossed cylinder lenses 26 and 27 mounted in a cylinder lens assembly of the type disclosed in U.S. Pat. No. 3,498,699, which patent is incorporated herein by reference in its entirety. It thus includes a pair of crossed cylinder lens discs 28 and 30 shown in FIG. 2. The forward disc 28 carries weak crossed cylinder lenses 26 and the rear disc 30 carries the strong crossed cylinder lenses 27.

The strong and weak crossed cylinder discs 28 and 30 carry sets of strong and weak crossed cylinder lenses of various powers mounted circumferentially on the discs, so that a selected lens will, upon rotation of the discs, come into alignment with the viewing tube 24. Each disc 28 and 30 carries four lenses and has one open position 32 which is aligned with the viewing tube 24 when no crossed cylinder lens within such disc 28 or 30 is desired.

The crossed cylinder (X/CYL) lens powers utilized in the preferred embodiment are as follows:

| WEAK X/CYL LENSES MOUNTED IN WEAK DISC 28 | STRONG X/CYL LENSES MOUNTED IN STRONG DISC 30 |
| --- | --- |
| ±0.125 D | ±0.625 D |
| ±0.25 D | ±1.25 D |
| ±0.375 D | ±1.875 D |
| ±0.50 D | ±2.50 D |

The power of the combination of the weak and strong crossed cylinders 26 and 27 seen through the viewing tube 24 may be presented in a display 34 which indicates the total crossed cylinder lens power as seen through the viewing tube. For a positive or negative crossed cylinder refractor, the orientation of the plus axis of the weak and strong crossed cylinders 26 and 27 as seen through the viewing tube will be indicated on to the crossed cylinder axis scale 36. The designation of the positive or negative crossed cylinder refractor as seen in the display 34 may include the total crossed cylinder sphere power followed by the total crossed cylinder cylindrical power or the cylindrical power of the crossed cylinder. For a positive crossed cylinder refractor, the cylindrical power value is black in the display 34 with or without the sphere power in red. For a negative crossed cylinder refractor, the cylinder power in display 34 value is red with or without the sphere power in black. By convention, black designates positive lenses and red negative lenses.

A suitable structure for accomplishing the desired objective of mounting crossed cylinder lenses 26 and 27 so that they may be selectively positioned in line with viewing tube 24 and may be rotated is disclosed in U.S. Pat. No. 3,498,699, mentioned above, particularly at columns 5 and 6.

As will be readily appreciated, the described arrangement permits the refractionist to control not only the total power of the crossed cylinder lenses 26 and 27 in alignment with the viewing tube 24 (by means of crossed cylinder power know 37), but also the orientation of the axis of these lenses 26 and 27 (by means of cylinder axis rotation knob 39).

The described selectable crossed cylinder lens assembly makes possible the following crossed cylinder powers:

| WEAK X-CYL LENS IN WEAK DISC 28 | STRONG X-CYL LENS IN STRONG DISC 30 | DISPLAY X-CYL** (expressed in sphere plus cylinder notation) |
| --- | --- | --- |
| 0.00 | 0.00 | 0.00* |
| ±0.125 | 0.00 | 0.12/0.25 |
| ±0.25 | 0.00 | 0.25/0.50* |
| ±0.375 | 0.00 | 0.37/0.75* |
| ±0.50 | 0.00 | 0.50/1.00* |
| 0.00 | ±0.625 | 0.62/1.25 |
| ±0.125 | ±0.625 | 0.75/1.50 |
| ±0.25 | ±0.625 | 0.87/1.75 |
| ±0.375 | ±0.625 | 1.00/2.00 |
| ±0.50 | ±0.625 | 1.12/2.25 |
| 0.00 | ±1.25 | 1.25/2.50 |
| ±0.125 | ±1.25 | 1.37/2.75 |
| ±0.25 | ±1.25 | 1.50/3.00 |
| ±0.375 | ±1.25 | 1.62/3.25 |
| ±0.50 | ±1.25 | 1.75/3.50 |
| 0.00 | ±1.875 | 1.87/3.75 |
| ±0.125 | ±1.875 | 2.00/4.00 |
| ±0.25 | ±1.875 | 2.12/4.25 |
| ±0.375 | ±1.875 | 2.25/4.50 |
| ±0.50 | ±1.875 | 2.37/4.75 |
| 0.00 | ±2.50 | 2.50/5.00 |
| ±0.125 | ±2.50 | 2.62/5.25 |

-continued

| WEAK X-CYL LENS IN WEAK DISC 28 | STRONG X-CYL LENS IN STRONG DISC 30 | DISPLAY X-CYL** (expressed in sphere plus cylinder notation) |
|---|---|---|
| ±0.25 | ±2.50 | 2.75/5.50 |
| ±0.375 | ±2.50 | 2.87/5.75 |
| ±0.50 | ±2.50 | 3.00/6.00 |

**For a + crossed cylinder refractor 0.12/0.25 is displayed as: 0.12 red 0.25 black
For a − crossed cylinder refractor 0.12/0.25 is displayed as: 0.12 black 0.25 red
*Crossed cylinder powers to be used for scanning for astigmatism as further described below.

SYNCHRONIZED VARIABLE CROSSED CYLINDER ASSEMBLY

Figure 3:
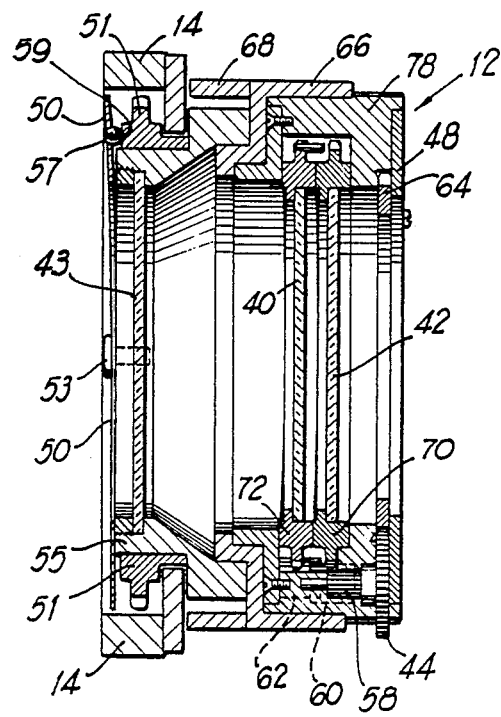
FIG. 3 is an enlarged cross-sectional view of the synchronized variable crossed cylinder structure taken along the lines 3—3 of FIG. 1.

The synchronized, variable, rotatable, three-lens crossed cylinder attachment or assembly 12 of the present invention (FIGS. 1, 2, 3 and 4) includes counter rotating lenses 40 and 42, and lens 43 which is stationary within assembly 12 (FIG. 3). Lenses 40 and 42 are cylinder lenses of equal power, each of which has a power equal to one-half of the power of stationary lens 43 of opposite sign. All lenses 40, 42 and 43 may alternatively be crossed cylinder lenses of appropriate power. For instance, stationary lens 43 may be a −3.00 D cylinder while rotating lenses 40 and 42 are each a +1.50 D cylinder for a positive crossed cylinder assembly. Similarly stationary lens 43 may be a ±1.50 D cross cylinder lens while rotating lenses 40 and 42 are each ±0.75 D crossed cylinders. Likewise, the stationary lens 43 may be a +3.00 D cylinder while rotating lenses 40 and 42 are each a −1.50 D cylinder.

Figure 4:
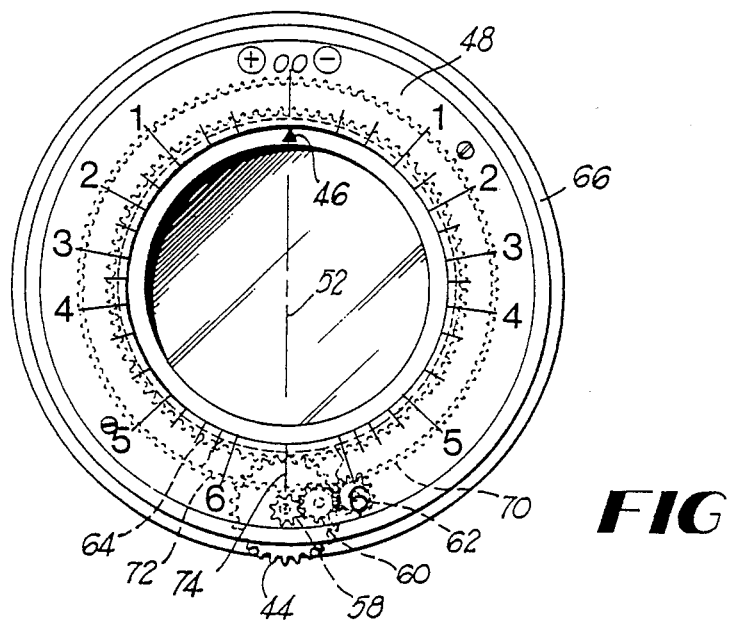
FIG. 4 is an enlarged front view of the synchronized variable crossed cylinder assembly of the present invention with gears shown in phantom lines.

Referring to FIG. 4, when the thumb wheel 44 of the assembly 12 is turned, the two rotating lenses 40 and 42 will rotate in opposite directions to each other at an equal rate relative to a stationary combined lens axis. The combined lens axis will always bisect the angle formed by (a) the axes of lenses 40 and 42 (if cylinder lenses are used), or (b) the negative axes or the positive axes of lenses 40 and 42 (if crossed cylinder lenses are used). The resulting power of the assembly 12 will be indicated by the position of pointer 46 on scale 48 on the front of assembly 12. The power of the combined lenses 40, 42 and 43 will be zero when their axes are parallel (when cylinder lenses are used) and zero when the positive axes of lenses 40 and 42 are parallel to the negative axis of lens 43.

The assembly 12 is attached to a yoke or turret 14 to swing it between a position in alignment with the viewing tube 24 and a position clear of the tube 24 (as is illustrated in FIG. 1). This may be accomplished by utilizing the turret structure described in U.S. Pat. No. 3,498,699, particularly at columns 6–8, for mounting a Jackson crossed cylinder and a rotary prism loupe.

The axis 52 of the synchronized variable crossed cylinder assembly 12 must be maintained parallel to the axis 54 of the lenses 26 and 27 in the selectable crossed cylinder lens assembly 22 (or parallel to the axis of cylinder lenses so mounted if the crossed cylinder lens assembly 22 of the present invention is not used), and such axes must be simultaneously controlled by the cylinder axis rotation knob 39. This may be accomplished by utilizing the structure disclosed in U.S. Pat. No. 3,498,699 for setting the cylinder axis parallel with the cross cylinder flip axis of the Jackson crossed cylinder structure disclosed therein.

A substantially suitable structure for synchronized variable crossed cylinder lens attachment may be provided by mounting stationary lens 43 in loupe 55 and by substituting lenses 40 and 42 in place of the prisms normally used in a conventional Risley rotary prism loupe attachment and by recalibrating the scale on the face of the Risley prism attachment. The modified Risley prism attachment may be mounted as illustrated in FIGS. 3 and 4 on the loupe 55, which corresponds to loupe 158 of the Jackson crossed cylinder loupe assembly described in U.S. Pat. No. 3,498,699. This modified Risley prism loupe structure and its linkage by means of the conventional Jackson crossed cylinder loupe mount to the cylinder axis controlling mechanism of a conventional refractor will provide the mechanics required for the synchronized variable crossed cylinder lens attachment 12 of the present invention. Optimal operation may be achieved, however, by gearing modification to utilize a greater arc in the scale 48. Ideally, pointer 46 should rotate 180° or slightly less at the same time the axes of lenses 40 and 42 rotate 180° to each other (90° with respect to the axis of lens 43). This will provide the least crowded scale 48 possible.

The expanded range of cylinder powers possible utilizing the three-lens system of the assembly 12 described here, as compared to a pair of counter-rotating equal but opposite power cylinder lenses, (or equal crossed cylinder lenses), as described in my previous application, may be understood by comparison of the two types of lens systems. First a system containing equal power but opposite sign cylinders in accordance with the teaching of my previous applications:

| CHART 1 | |
|---|---|
| Clockwise rotating lens | 0.00 − 3.00 × 180° |
| Counter rotating lens | 0.00 + 3.00 × 180° |

RESULTANT CROSSED CYLINDER AS GENERATED WITH ABOVE CYLINDERS FOR VARIOUS DEGREES OF ANGULAR ROTATION

| OFF-AXIS ROTATION (Deg.) | RESULTANT CROSSED CYLINDERS APPROXIMATE (EXACT) |
|---|---|
| 1 | 0.25 (−0.10 + 0.21 × 45°) |
| 2 | 0.50 (−0.21 + 0.42 × 45°) |
| 5 | 1.00 (−0.52 + 1.04 × 45°) |
| 10 | 2.00 (−1.03 + 2.05 × 45°) |
| 15 | 3.00 (−1.50 + 3.00 × 45°) |
| 18 | 3.50 (−1.76 + 3.53 × 45°) |
| 21 | 4.00 (−2.01 + 4.01 × 45°) |
| 24 | 4.50 (−2.23 + 4.46 × 45°) |
| 28 | 5.00 (−2.49 + 4.97 × 45°) |
| 33 | 5.50 (−2.74 + 5.48 × 45°) |
| 45 | 6.00 (−3.00 + 6.00 × 45°) |

Next, the three lens system of the present invention:

| CHART 2 | |
|---|---|
| Stationary lens | 0.00 − 3.00 × 180° |
| Rotatable lens | 0.00 + 1.50 × 180° |
| Rotatable lens | 0.00 + 1.50 × 180° |

RESULTANT CROSSED CYLINDER POWER AS GENERATED WITH ABOVE LENS COMBINATION

| OFF-AXIS ROTATION (Deg.) | RESULTANT CROSSED CYLINDER APPROXIMATE (EXACT) |
|---|---|
| 17 | 0.50 (−0.25 + 0.51 × 90°) |
| 21 | 0.75 (−0.38 + 0.77 × 90°) |
| 24 | 1.00 (−0.49 + 0.99 × 90°) |
| 27 | 1.25 (−0.62 + 1.24 × 90°) |
| 30 | 1.50 (−0.75 + 1.50 × 90°) |
| 33 | 1.75 (−0.89 + 1.78 × 90°) |
| 35 | 2.00 (−0.98 + 1.97 × 90°) |
| 38 | 2.25 (−1.13 + 2.27 × 90°) |

-continued

| | |
|---|---|
| 40 | 2.50 (−1.24 + 2.48 × 90°) |
| 43 | 2.75 (−1.39 + 2.79 × 90°) |
| 45 | 3.00 (−1.50 + 3.00 × 90°) |
| 50 | 3.50 (−1.76 + 3.52 × 90°) |
| 55 | 4.00 (−2.01 + 4.03 × 90°) |
| 60 | 4.50 (−2.25 + 4.50 × 90°) |
| 75 | 5.00 (−2.46 + 4.93 × 90°) |
| 84 | 5.50 (−2.77 + 5.54 × 90°) |
| 90 | 6.00 (−3.00 + 6.00 × 90°) |

Figure 5:
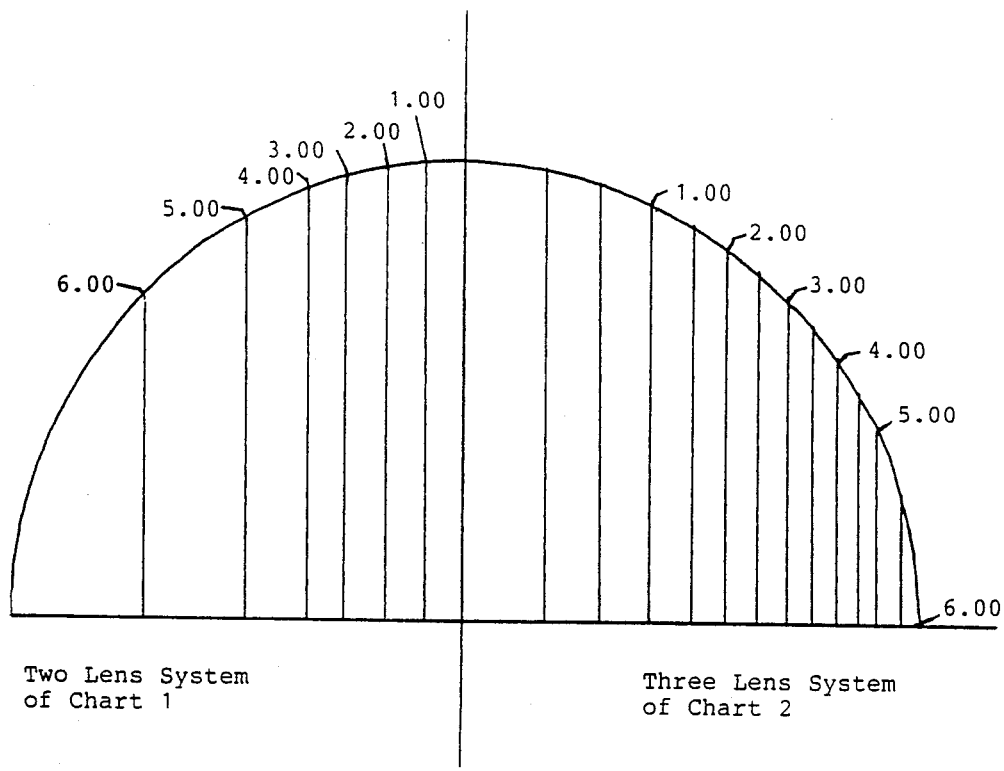
FIG. 5 is a graphic illustration of the expanded range of cylinder lens powers provided by the present invention as compared to a two-lens crossed cylinder lens assembly.

Charts 1 and 2 are illustrated graphically in FIG. 5. As can be seen from FIG. 5, the entire range of powers is expanded, particularly at the upper and lower ends.

Mounting of the modified Risley prism attachment is accomplished by mounting housing 78 on a cup 66, which in turn is seated on loupe 55. As one skilled in the art will readily appreciate, cup 66 may be any convenient shape which provides mating between housing 78 and loupe 55. A tubular shield 68 having the same outer diameter as cup 66 may be mounted around loupe 55 with a set screw or other convenient means to provide an attractive outer appearance for assembly 12.

FIG. 4 is a front view of the synchronized variable crossed cylinder lens assembly 12 constructed from a modified Risley prism attachment. The rotary thumb wheel 44 with its underlying gear of a smaller diameter 58 is the drive system which rotates ring gear driving gears 60 and 62. Thumb wheel gear 58 rotates driving gear 60, which rotates ring gear 70 (in which lens 42 is mounted) and driving gear 62. Gear 62 in turn rotates ring gear 72, in which lens 40 is mounted, at an equal rate but in the opposite site direction from ring gear 70. This is accomplished because driving gear 60 meshes with the front crossed cylinder lens 42 ring gear 70 and driving gear 62 meshes with the rear crossed cylinder lens 40 ring gear 72.

Rotary thumb wheel 44 also rotates pointer ring gear 64 which carries pointer 46. Pointer 46 indicates the combined power of lenses 40, 42 and 43 on scale 48, which is mounted on housing 78. Alternatively, thumb wheel 44 could drive intermediate gears of appropriate diameter, which would in turn drive pointer ringer gear 64 in order to modify the rate at which pointer ring gear 64 rotates relative to rotation of lenses 40 and 42, as described above.

OPERATIONS

A refractor modified in accordance with the present invention may be used by first using the spherical lens in sphere lens assembly 20 to produce a fog. With the patient either wearing or not wearing his glasses and observing the smallest discernible visual acuity line, this fog is then reduced in 0.25D steps in order to determine the spherical equivalent. The typical patient responses to such fog reduction would be: blurred—clear—sharper and darker. The "blurred" response would typically represent a 0.50D fog, the "clear" response a 0.25D fog and the "sharper and darker" response the spherical equivalent.

The synchronized variable crossed cylinder assembly 12 is then rotated in line with the viewing tube 24. The spherically precorrected eye is then offered various crossed cylinder powers by turning the thumb wheel 44, with the cylinder axis 36 set at 180°. If there is no improvement in the spherical precorrected visual acuity, the cylinder axis knob 39 is rotated into the vertical and oblique meridians and the crossed cylinder power scanning technique is repeated as described.

This allows the refractionist to scan the visual acuity field in 45° intervals by only rotating the crossed cylinder axis 52 by means of knob 37 and turning the thumb wheel 44. The refractionist also may scan 30° intervals or start at any of the four quadrants and then scan the four 45° quadrants. With this scanning technique, the patient is shown several hundred sets of perfect crossed cylinders. If there is no improvement in the spherical preconditioned eye, the distant refraction for that eye is then complete. The identical procedure is then repeated for the other eye followed by the routine determination of the phorias and reading add. This is the routine for a stigmatic patient.

For an astigmatic patient, the spherical preconditioned eye would enjoy an improvement in the distant visual acuity in one of the quadrants scanned using the 45° or 30° scanning techniques as the crossed cylinder power is increased or decreased to produce the optimal vision. When the proper crossed cylinder power is determined, the synchronized crossed cylinder axis 52 is rotated clockwise and counter-clockwise by means of knob 39 to produce the least non-distorted clear vision. After the proper refractive axis of the patient is determined through the patient's responses, the final power of the synchronized crossed cylinder assembly is increased or decreased to produce the optimal visual acuity. The final refractive error is the sum of the sphere power of the sphere lens assembly 20 and the power of synchronized crossed cylinder attachment 12 displayed on scale 48 designated axis 52 displayed on axis scale 36.

An alternative to neutralizing astigmatism with the synchronized variable crossed cylinder lens attachment 12 is to dial predetermined crossed cylinder powers into the viewing tube 24 by turning the crossed cylinder power knob 37 to the same power setting as the variable attachment 12. The attachment 12 is then rotated out of the field of the viewing tube 24. Stronger or weaker crossed cylinders 26 are then selected by rotating disks 28 and 30 by means of cylinder selector knob 37 to produce the optimal vision for the astigmatic patient after the proper axis has been determined as described in the previous paragraph. It should be noted that it is very important to overcorrect the astigmatism correction in order to show the patient a new image he has not seen and then reduce the blurred overcorrected image in ±0.125D crossed cylinder steps to produce the optimal visual acuity.

Another alternative for the detection and neutralization of astigmatism is to utilize crossed cylinder lens powers of ±0.25D, ±0.375D, or ±0.50D in the selectable crossed cylinder lens assembly 22 to scan for astigmatism. The patient is allowed to compare his spherical preconditioned visual acuity and 0.00D crossed cylinder power in the viewing tube to ±0.25D crossed cylinder power in the viewing tube. If there is no improvement in the visual acuity, cylinder axis rotation knob 39 is rotated 30° or 45°, depending on the refractionist's preference, and the procedure repeated. If the visual acuity is improved with 0.00D crossed cylinder power in the viewing tube in all 30° or 45° meridians as compared to the ±0.25D lens, there is no astigmatism. It is rarely necessary to use the ±0.125D crossed cylinder for an astigmatic eye scan. If there is an improvement with the ±0.25D lens at a certain meridian, the power of the crossed cylinder is increased and/or decreased to produce the optimal visual acuity, after which the crossed cylinder axis 54 is rotated in a clockwise and counterclockwise manner by means of axis knob 39 to produce the clearest nondistorted vision. The final crossed cylinder power is then checked. If the refractionist suspects a nondiscriminating patient or moderate astigmatism, he may scan with crossed cylinders of larger powers ±0.375D or ±0.50D).

The axis may be checked by overcorrecting the final crossed cylinder power (the one giving the patient his best visual acuity as determined in the preceding paragraph) ±0.125D crossed cylinder by using either the synchronized rotary crossed cylinder attachment 12 or by dialing in the appropriate lens in selectable lens assembly 22. The corrected crossed cylinder power as viewed through the viewing tube 24 is then rotated in a clockwise and a counter clockwise manner to an axis which gives the his best non-distorted vision. After the exact axis is chosen by the patient (that which gives him the best non-distorted vision), the added ±0.125D crossed cylinder is removed.

The final crossed cylinder power may be checked with the synchronized variable crossed cylinder assembly 12 device if te astigmatic patient was initially neutralized with the selectable crossed cylinder assembly 22 of the present invention. This is important in order to eliminate mechanical and auditory error during refraction. Likewise, the patient may be checked with the selectable crossed cylinder assembly 22 if first refracted by the synchronized variable crossed cylinder assembly 12.

My invention is not limited to the embodiments described and represented above, and various modifications can be made without departing from the scope and spirit of the preceding description and the following claims.

I claim:

1. A refractor, comprising a pair of batteries, each battery comprising a viewing tube, selectable sphere lenses, and a variable, three-lens crossed cylinder lens assembly comprising a stationary cylinder lens and two identical cylinder lenses concurrently alignable with the viewing tube, each identical cylinder lens of power equal to one-half the stationary lens power and of opposite sign, mounted in a means for rotating them in opposite directions at the same rate relative to a combined lens axis.

2. A refractor in accordance with claim 1, wherein the variable crossed cylinder lens assembly is mounted on a turret for movement between a position in which the lenses are in alignment with the viewing tube and a position in which the assembly is clear of the viewing tube, and is rotatable to permit rotation of the combined lens axis.

3. A refractor in accordance with claim 2, further comprising:
   a. means for positioning in alignment with the viewing tube a selected crossed cylinder lens having a positive axis and a negative axis and means for rotating the selected crossed cylinder lens so positioned; and
   b. means for positioning the variable crossed cylinder lens assembly combined lens axis parallel to one of the positive or negative axes of the selected crossed cylinder lens and maintaining such parallel relationship during rotation of the selected crossed cylindered lens.

4. A refractor in accordance with claim 2, wherein the variable crossed cylinder lens assembly rotating means comprises a thumbwheel acting on two cells in which one of each of the two identical lenses are mounted.

5. A refractor, comprising a pair of batteries, each battery comprising:
   a. a viewing tube,
   b. a selectable crossed cylinder lens assembly, the assembly comprising at least one lens-carrying crossed cylinder disk carrying a plurality of graded crossed cylinder lenses,
   c. a means for rotating the disk whereby any selected one crossed cylinder lens in the disk may be positioned in alignment with the viewing tube, and
   d. a variable, three-lens crossed cylinder lens assembly comprising a stationary cylinder lens and two identical cylinder lenses concurrently alignable with the viewing tube, each identical cylinder lens of power equal to one-half the stationary lens power and of opposite sign, mounted in means for rotating them in opposite directions at the same rate relative to a combined lens axis.

6. A refractor in accordance with claim 5, each battery further comprising:
   e. a means for rotating each graded crossed cylinder lens, and
   f. a means for positioning the combined lens axis parallel to one of the positive or negative axes of the selected crossed cylinder lens and maintaining such parallel relationship during rotation of the selected crossed cylinder lens.

7. A refractor in accordance with claim 6, each battery further comprising:
   g. a means for alternatively positioning the variable crossed cylinder lens assembly in alignment with the viewing tube or clear of the viewing tube.

8. A refractor in accordance with claim 7, wherein the variable, three-lens crossed cylinder lens assembly rotating means comprises a thumb wheel acting on two cells in each of which one of the two lenses is mounted.

9. A refractor in accordance with claim 5, each battery further comprising a sphere lens assembly.

10. A refractor, comprising a pair of batteries, each battery comprising:
    a. a viewing tube,
    b. a selectable sphere lens assembly comprising at least one lens-carrying disk carrying a plurality of graded sphere lenses and a means for rotating the disk whereby any selected one sphere lens in the disk may be positioned in alignment with the viewing tube,
    c. a selectable crossed cylinder lens assembly comprising at least one lens-carrying crossed cylinder disk carrying a plurality of graded crossed cylinder lenses and a means for rotating the disk whereby any selected one crossed cylinder lens in the disk may be positioned in alignment with the viewing tube,
    d. a variable, three-lens crossed cylinder lens assembly mounted on a turret for movement between a position in which the assembly is in alignment with the viewing tube and a position in which the assembly is clear of the viewing tube, which assembly comprises a stationary cylinder lens and two identical cylinder lenses concurrently alignable with the viewing tube, each identical cylinder lens of power equal to one-half the stationary lens power and of opposite sign, mounted in a means for rotating them utilizing a thumb wheel acting on two cells in each of which one of the two rotatable lenses are mounted to rotate in opposite directions at the same rate relative to a combined lens axis, e. a means for rotating the selected crossed cylinder lens positioned in alignment with the viewing tube, and f. a means for positioning the combined lens axis of the variable, three-lens assembly parallel to one of the positive or negative axes of the selected crossed cylinder lens, and a means for maintaining the respective parallel relationship during rotation of the selected crossed cylinder lens by simultaneously rotating the variable, three-lens crossed cylinder lens assembly.

11. A refractor, comprising a pair of batteries, each battery comprising a viewing tube, selectable sphere lenses, and a variable, three-lens crossed cylinder lens assembly comprising a stationary crossed cylinder lens and two identical crossed cylinder lenses concurrently alignable with the viewing tube, each identical crossed cylinder lens of power equal to one-half the stationary lens power, mounted in a means for rotating them in opposite directions at the same rate relative to a combined lens axis.

12. A refractor in accordance with claim 11, wherein the variable crossed cylinder lens assembly is mounted on a turret for movement between a position in which the lenses are in alignment with the viewing tube and a position in which the assembly is clear of the viewing tube, and is rotatable to permit rotation of the combined lens axis.

13. A refractor in accordance with claim 12, further comprising:

a. means for positioning in alignment with the viewing tube a selected crossed cylinder lens having a positive axis and a negative axis and means for rotating the selected crossed cylinder lens so positioned; and b. means for positioning the variable crossed cylinder lens assembly combined lens axis parallel to one of the positive or negative axes of the selected crossed cylinder lens and maintaining such parallel relationship during rotation of the selected crossed cylindered lens.

14. A refractor in accordance with claim 12, wherein the variable crossed cylinder lens assembly rotating means comprises a thumbwheel acting on two cells in which one of each of the two identical lenses are mounted.

15. A refractor, comprising a pair of batteries, each battery comprising:

a. a viewing tube, b. a selectable crossed cylinder lens assembly, the assembly comprising at least one lens-carrying crossed cylinder disk carrying a plurality of graded crossed cylinder lenses, c. a means for rotating the disk whereby any selected one crossed cylinder lens in the disk may be positioned in alignment with the viewing tube, and d. a variable, three-lens crossed lens assembly comprising a stationary crossed cylinder lens and two identical crossed cylinder lenses concurrently alignable with the viewing tube, the identical crossed cylinder lenses having a combined power equal to the stationary lens power and mounted in a means for rotating them in opposite directions at the same rate relative to a combined lens axis.

16. A refractor in accordance with claim 15, each battery further comprising:

e. a means for rotating each graded crossed cylinder lens, and f. a means for positioning the combined lens axis parallel to one of the positive or negative axes of the selected crossed cylinder lens and maintaining such parallel relationship during rotation of the selected crossed cylinder lens.

17. A refractor in accordance with claim 16, each battery further comprising:

g. a means for alternatively positioning the variable crossed cylinder lens assembly in alignment with the viewing tube or clear of the viewing tube.

18. A refractor in accordance with claim 17, wherein the variable crossed cylinder lens assembly rotating means comprises a thumb wheel acting on two cells in each of which one of the two lenses is mounted.

19. A refractor in accordance with claim 18, each battery further comprising a sphere lens assembly.

20. A refractor, comprising a pair of batteries, each battery comprising:

a. a viewing tube, b. a selectable sphere lens assembly comprising at least one lens-carrying disk carrying a plurality of graded sphere lenses and a means for rotating the disk whereby any selected one sphere lens in the disk may be positioned in alignment with the viewing tube, c. a selectable crossed cylinder lens assembly comprising at least one lens-carrying crossed cylinder disk carrying a plurality of graded crossed cylinder lenses and a means for rotating the disk whereby any selected one crossed cylinder lens in the disk may be positioned in alignment with the viewing tube, d. a variable, three-lens crossed cylinder lens assembly mounted on a turret for movement between a position in which the variable crossed cylinder lenses are in alignment with the viewing tube and a position in which the assembly is clear of the viewing tube, which assembly comprises a stationary crossed cylinder lens and two identical crossed cylinder lenses concurrently alignable with the viewing tube, the identical crossed cylinder lenses having a combined power equal to the stationary lens power and mounted in a means for rotating them utilizing a thumb wheel acting on two cells in each of which one of the two lenses are mounted to rotate in opposite directions at the same rate relative to a combined lens axis, e. a means for rotating the selected crossed cylinder lens positioned in alignment with the viewing tube, and f. a means for positioning the combined lens axis parallel to one of the positive or negative axes of the selected crossed cylinder lens, and a means of maintaining the respective parallel relationship during rotation of the selected crossed cylinder lens by simultaneously rotating the variable, three-lens crossed cylinder lens assembly.

21. A method of refracting an eye of a patient utilizing a refractor, comprising the steps of:

a. determining the spherical component of the refractive error of the eye and placing a sphere lens of power appropriate to correct such spherical refractive error in the optical path of the eye;

b. placing a variable, three-lens crossed cylinder lens assembly having a combined lens axis and comprising one stationary and two counter rotating lenses, each having a cylinder component, in the optical path of the eye with the combined lens axis of the lens assembly in a first position;

c. varying the power of the variable crossed cylinder assembly by counter rotating the two lenses and noting the patient's response thereto; and d. rotating the combined lens axis of the variable crossed cylinder lens assembly a predetermined increment and repeating step (c).

* * * * *